US005593973A

United States Patent [19]
Carter

[11] Patent Number: 5,593,973
[45] Date of Patent: *Jan. 14, 1997

[54] TREATMENT OF VIRAL HEPATITIS WITH MISMATCHED DSRNA

[75] Inventor: William A. Carter, Birchrunville, Pa.

[73] Assignee: Hemispherx Biopharma Inc., Philadelphia, Pa.

[ * ] Notice: The term of this patent shall not extend beyond the expiration date of Pat. No. 5,132,292.

[21] Appl. No.: 318,514

[22] Filed: Oct. 5, 1994

Related U.S. Application Data

[63] Continuation of Ser. No. 158,357, Nov. 29, 1993, abandoned, which is a continuation of Ser. No. 967,579, Oct. 27, 1992, abandoned, which is a continuation of Ser. No. 713,003, Jun. 10, 1991, abandoned, which is a continuation of Ser. No. 560,273, Jul. 30, 1990, abandoned, which is a continuation of Ser. No. 237,018, Aug. 26, 1988, abandoned, which is a continuation-in-part of Ser. No. 93,523, Sep. 4, 1987, abandoned.

[51] Int. Cl.⁶ .............................. A61K 31/70; C12Q 1/68
[52] U.S. Cl. .................. 514/44; 435/6; 536/23.1
[58] Field of Search ................ 435/6, 51.1, 240.2; 514/44; 536/23.1, 25.6

[56] References Cited

U.S. PATENT DOCUMENTS

| 4,024,222 | 5/1977  | Tsó et al. ...... 424/180 |
| 4,130,641 | 12/1978 | Tsó et al. ...... 424/85 |
| 4,400,375 | 8/1983  | Douthart et al. ...... 424/85 |
| 4,795,744 | 1/1989  | Carter ...... 514/44 |
| 4,820,696 | 4/1989  | Carter ...... 514/44 |
| 5,132,292 | 7/1992  | Carter ...... 514/44 |

FOREIGN PATENT DOCUMENTS

| 0113162 | 7/1984  | European Pat. Off. . |
| 0213921 | 3/1987  | European Pat. Off. . |
| 0285263 | 10/1988 | European Pat. Off. . |
| 0299775 | 1/1989  | European Pat. Off. . |
| 0308066 | 3/1989  | European Pat. Off. . |

OTHER PUBLICATIONS

*Biological Effects of Polynucleotides*, R. F. Beers and W. Braun (editors), Springer–Verlag, New York, 1971, Phillips et al, "Polyinosinic–Polycytidylic Acid Toxicity", pp. 259–273.

Carter et al, The Lancet, 1/8545, pp. 1286–1292, Jun. 6, 1987.

Strayer, Proceedings of the Annual Meeting of the American Society of Clinical Oncology, vol. 7, p. 2, abstract A6, Mar., 1988.

Carter et al, Proceedings of the Annual Meeting of the American Society of Clinical Oncology, vol. 6, p. 2, abstract A8, Mar., 1987.

Brodsky et al, Journal of Biological Response Modifiers, vol. 4, pp. 669–675, 1985.

Wu et al, AIDS Research, vol. 2, No. 2, pp. 127–131, 1986.

Wreschner et al, Nucleic Acids Research, vol. 9, No. 7, pp. 1571–1581, 1981.

Zullo et al, Cell, vol. 43, pp. 793–800, 1985.

Cayley et al, European J. Biochemistry, vol. 143, pp. 165–174, 1984.

Hilleman, Archives of Internal Medicine, vol. 126, pp. 109–124, 1970.

De Benedetti et al, Proceeding of the National Academy of Science (USA), vol. 84, pp. 658–662, Feb. 1987.

Feldman et al. Voym Virusol. 29: 463–468 (1984).

Falcoff et al. Antimicro. Agent Chemo. 3:590–598 (1973).

*Primary Examiner*—John L. Leguyader
*Attorney, Agent, or Firm*—Nixon & Vanderhye

[57] ABSTRACT

Hepatitis viral infections are efficaciously treated with mismatched dsRNAs, notably $rI_n \cdot r(C_{11-14},U)_n$.

3 Claims, 4 Drawing Sheets

TREATMENT OF VIRAL HEPATITIS WITH MISMATCHED DSRNA

CROSS-REFERENCE TO RELATED APPLICATION

This application is a continuation of application Ser. No. 08/158,357 filed Nov. 29, 1993, now abandoned, which is a continuation of 07/967,579, filed Oct. 27, 1992, now abandoned, which is a continuation of 07/713,003, filed Jun. 10, 1991, now abandoned, which is a continuation of 07/560,273, filed Jul. 30, 1990, now abandoned, which is a continuation of 07/237,018, filed Aug. 26, 1988, now abandoned, which is a continuation-in-part of 07/093,523, filed Sep. 4, 1987, now abandoned.

This invention relates to diagnosing a dsRNA deficiency state and procedures to supply exogenous dsRNA of appropriate molecular configuration to restore it to a normal level.

BACKGROUND OF THE INVENTION

New methods in diagnosis and therapy of viral diseases, chronic pathogen infections generally and cancer emerge when the diverse roles in host defense played by natural dsRNA are uncovered. For example, development of AIDS (a retroviral infection/cancer) is associated with progressively severe dysfunction in biological processes which I have found to be catalyzed by dsRNA including not only interferon biosynthesis, but also bioactive 2-5A production, RNase L activity and various cell-mediated immune functions. I show that specific reduction in bioactive dsRNA, or enzymes which depend on dsRNA, within specific cells contributes to disease progression.

A deficiency state in pathways involving bioactive dsRNA also lies at the core of various cellular lesions in host defense systems leading to death. Earlier, I detected an inhibitor of RNase L in lymphocytes of HIV-infected ARC and AIDS patients which is just one result (from many) of inadequate intracellular dsRNA levels. Therapy with appropriately configured synthetic dsRNA eliminates this inhibitor(s), which can explain part of the clinical responses I observed with respect to reduction in virus concentration and restoration of immune function in patients with a variety of chronic viremias which at present continue to largely defy definitive medical intervention. Accordingly, I have now developed an integrative invention which can explain, quantitate, and correct a variety of dsRNA deficiency states in varied disease settings. I have also discovered that certain dsRNAs, e.g., mismatched dsRNA, can actually substitute for a naturally occuring dsRNA which help maintain functions essential for normal cell processes. The absence of such dsRNA regulation, if not corrected with a suitable exogenous dsRNA, can cause various abnormal cellular processes to develop. Abnormal cellular processes then lead to chronic viral or other intracellular pathogen infections, reduced immune cell functions and, ultimately, chronic morbidity and possibly death itself.

Clinical Strategies. Viral infections can often follow partial disturbance of the immune system through agents as diverse as stress and viruses which directly attack immune function. For example, AIDS (Acquired Immune Deficiency Syndrome) follows the progressive deterioration of the immune system caused by infection of T lymphocytes by human immunodeficiency virus, HIV (Coffin et al., *Science* vol. 232, p. 697, 1986).

For completeness, it should be noted that different designators for the HIV virus exist; LAV is the designator for the AIDS virus isolated at the Pasteur Institute, Paris, France and HTLV-III is the designator for the AIDS virus isolated at the National Institute of Health, Bethesda, Md., U.S.A. Currently, HIV is used as a generic term for the virus. Frequently in this text, the HIV virus will be referred to generically or designated HIV or HTLV-III or LAV without intending to differentiate between them. Furthermore, the term HIV in the specification and claims includes all other viruses which may be associated with producing AIDS, whether yet isolated or not.

HIV infection is a progressive disease although the rate of transition from one phase to another is variable. Asymptomatic individuals infected by HIV can develop a condition (LAS or pre-ARC) characterized by lymphadenopathy. Patients progress to AIDS-related complex or ARC by exhibiting the T4 cell deficit and later show reduced ability of lymphocytes to undergo antigen-stimulated proliferation and IFN-gamma production. These patients lose various cell mediated immune functions such as delayed cutaneous hypersensitivity, eventually becoming completely anergic. They exhibit evidence of breakdown in host defense mechanisms including Herpes Zoster infections, oral candidiasis (thrush), and symptoms such as prolonged fevers, night sweats diarrhea and weight loss. Finally, these patients experience certain severe opportunistic infections (e.g., *Pneumocystis carinii* pneumonia) and are then defined as having full-blown AIDS, with an approximately 50% mortality within 12 months. The HIV virus infection is chosen as an illustrative case simply because the level of dsRNA deficiency is so pronounced. Many other diseases, including indolent viral infections, will be associated with similar deficiencies; thus, my invention has unexpected wide applicability.

Importantly, the typical progression outlined above does not describe the remarkable disparity in clinical symptomatology among HIV-infected patients or many other patients with chronic disease such as Epstein Barr or EB infection, hepatitis virus infection, cytomegalovirus, herpes infections, etc. Components of the immune system decay with vastly different rates in various patients and the lack of bioactive dsRNA is a cause or contributing factor in this process. HIV infection may develop in a variety of different types of cells (e.g., blood cells, glial cells). Some patients develop neurological dysfunction as their first symptom. Thus, various individuals may have vastly different therapeutic requirements even though all will probably require HIV eradication from T4 cells.

Two general pathological features need to be addressed in many different viral infections including those of ARC patients: a collection of immune deficits and ongoing viral infection (reviewed in Fauci, *Proc. Nat'l. Acad. Sci. USA*, vol. 83, p. 9278, 1986). Therapeutic intervention which attacks only the immune deficits but fails to control virus replication appears to be counterproductive especially when such treatment activates T4 cells. For example, T-helper cells with Tac receptors are responsive to the lymphokine IL-2. In AIDS victims, IL-2 causes expansion of HIV-sensitive cells and apparent worsening of the disease.

Attacking viral infections directly, e.g., the HIV infection, has met with some success especially evidenced by the viral reverse transriptase inhibitor designated azidothymidine (AZT) which can reduce HIV "load" in some patients and prolong life. Such therapy is not without undesirable results. In a minority of patients, AZT also causes temporary recovery of T-cell meditated immunity as measured by a transient rise in T4 cells and by appearance of delayed type hypersensitivity (Fischl et al. *New Eng. J. Med.*, July, 1987) However, reverse transcriptase inhibitors are toxic at doses needed to produce significant antiviral effects and are thus poorly tolerated over time. Antiviral agents may need to be administered for the life of the patient.

IFN is both ineffective as a general antiviral compound and as an anti-AIDS drug, probably because it is not an antidote for the dsRNA-relted defects which I have now uncovered. Certainly, ARC/AIDS victims have various "defects" in IFN pathways, such as the production of a defective, acid-labile IFN and inability of T4 cells to produce appropriate amounts of IFN gamma which are well described in the medical literature. Earlier, I concluded that these various IFN-related defects in ARC and AIDS patients may prove to be related in whole or part to a lack of normal RNase L (a terminal pathway mediator) activity in lymphocytes which I described in my copending application Ser. No. 021,372 filed Mar. 3, 1987, which is hereby incorporated by reference. Although dsRNA-dependent 2-5A synthetase is elevated in blood lymphocytes of individuals with ARC/AIDS as well as other chronic viremias, I have found that the same blood cells show diminished levels of authentic 2-5A and low RNase L (see below). I correlated the low RNase L activity with low quantities of $M_r$80,000 protein capable of binding a photoaffinity labeled analogue of 2-5A. My findings are consistent with a dsRNA pathway(s) which has (have) been shut down and the relative absence and/or inhibitor of RNase L.

Vaccination against HIV and other viruses, and the use of passive anti-HIV antibodies, are also under consideration for viral prevention and treatment, respectively, but may have significant limitations: for example, HIV (as well as influenza virus in particular) readily can infect cells covertly. I also described a role for dsRNA to enhance antibody formation against viruses in general and retroviruses in particular in the above-mentioned patent application.

I describe herein a new phenomenon that argues for double-stranded RNAs (dsRNA) to constitute the first group of molecules which are effective against both the viral and immune lesions of various subacute/chronic vital infections such as HIV and others. These defects can be corrected with laser-like precision without adversely affecting other bodily functions which is a common limitation of presently available therapies for chronic viral infections. I conclude that patients with unresolved and indolent viral infections often have specific defects in vital intracellular dsRNA-dependent pathways which can be reversed or ameliorated at least in part by an exogenously supplied dsRNA (this is explained graphically in the flow chart of FIG. 1), and that monitoring these pathways, before and during treatment, provides a novel efficacious manner to gauge the degree of dsRNA replacement therapy required an individual patient or specific disease basis.

Critical enzymes associated with host defense require dsRNAs for expressing bioactivity. These enzymes can be activated by exogenous dsRNA if the level of natural intracellular dsRNA is too low. Part of the pleiotropic action of dsRNA derives from its ability to induce the synthesis of the entire range of IFNs—alpha, beta and gamma—which operate through a group of intracellular mediators including a dsRNA-dependent protein kinase, dsRNA-dependent 2-5A synthetase and 2-5A-dependent RNase L. These dsRNA-dependent enzymes may carry out many biological activities attributable to IFN as reviewed by Lengyel (*Ann. Rev. Biochem.*, vol. 51, p. 251, 1882). For example, production of an antisense RNA which blocks expression of 2-5A-synthetase causes profound sensitivity of animal cells to infection by different viruses (Bendetti et al. *Prac. Natl. Acad. Sci USA*, vol. 84, p. 658, 1987). The dsRNA-activated protein kinase phosphorylates eIF2 which inhibits protein synthese; it also has proteolytic activity to degrade viral proteins. DsRNA-activated 2-5A synthetase synthesizes 2-5A which activate RNase L, a pathway which I suggest plays a crucial role both in the inhibition of various animal viruses and in cell growth control (escape from which may lead to tumor formation). 2'-5' oligoadenylic acids are unusual in that the normal 3',5'phosphodiester linkage characteristics of most dsRNA has been replaced by a novel phosphodiester bond with acquisition of new biological properties.

Antiviral Activity of dsRNA. dsRNA is a well-known inducer of an antiviral state (Marcus et al, *Nature*, vol. 66, p. 815, 1977). Similarly, poly(A):poly(U) generated an antiviral state without inducing IFN. But, prior to my current invention, it was not known that natural dsRNA regulators exist and, therefore, that actual dsRNA deficiency states are common in humans, particularly associated with pathogenic episodes (viral, fungal, protozoan, bacterial invasions, etc., especially those which have intracellular (human) presence as a valuable or necessary components of their life cycle).

Antiproliferative Activity of dsRNA. Earlier, I found (*J. IFN. Res.*, vol. 6, p. 373, 1986) that 42% of more than 100 fresh human tumor specimens, when studied in soft agar, showed a 50% or greater reduction in tumor cell colony formation after only one exposure to dsRNA. These cells are dsRNA deficient. I also described independent IFN and dsRNA sensitivity in various human tumor cell lines and found that human tumors propagated in nude mice were sensitive to dsRNA; dsRNA therapy was curative of some tumors (e.g., renal) and the animals lived to a normal life expectancy (see published European patent application 0,113,162). Herein, I report a strong correlation between clinical responses and dsRNA-dependent enzyme activation as opposed to detectable IFN or IL-2 induction secondary to dsRNA administration.

Immune Enhancement Activity of dsRNA. Earlier I reported (*J. Immunol.*, vol. 124, p. 1852, 1980) that dsRNA increased human natural killer NK cytlytic activity against human leukemia cells. The dsRNA structural requirements for NK augmentation paralleled those needed for 2-5A synthetase activation and for IFN induction.

Gene Control Mediated by dsRNA. Sullo et al (*Cell*, vol. 43, p. 793, 1985) demonstrated that dsRNA induces competence genes in resting fibroblasts including the oncogenes designated fos and myc. As used herein, "competence genes" are those genes in a cell whose actions are required in order to modulate vital actions such as multiplication, growth, etc. The IFN-beta gene induction by dsRNA may utilize a regulatory protein which is removed upon exposure of cells to dsRNA (Zinn et al. *Cell*, vol. 45, p. 611, 1986). I have determined that, to biological activity, exogenously supplied dsRNAs mimic a natural, nonviral, intracellular dsRNA such as heterogeneous nuclear RNA or mRNA complexed with poly(U). For example, I recently discovered an IFN-inducible dsRNA in Hela cell nuclei capable of activating 2-5A synthetase in vitro. The advent of cellular immunity far back in the evolutionary cycle in animals apparently set the stage for the evolution of IFN/dsRNA molecules toward implementing cellular differentiation, particularly differentiation promoted by IFN, I was able to achieve the more general insight that dsRNA can implement differentiation promoted by other regulatory proteins which set the stage for my definition of dsRNA deficiency states.

BRIEF DESCRIPTION OF THE DRAWINGS

FIG. 3 (parts A and B) is a photograph of polyacrylamide gel electrophoresis plates showing various zones and bands along each track.

DETAILED DESCRIPTION OF THE INVENTION

I describe herein a new phenomenon that argues for double-stranded RNAs (dsRNA) to constitute the first group of molecules which are effective against both the viral and immune lesions of various subacute/chronic viral infections such as HIV and others. These defects can be corrected with laser-like precision without adversely affecting other bodily functions which is a common limitation of presently available therapies for chronic viral infections. I conclude that patients with unresolved and indolent viral infections often have specific defects in vital intracellular dsRNA-dependent pathways which can be reversed or ameliorated at least in part by an exogenously supplied dsRNA (this is explained graphically in the flow chart of FIG. 1), and that monitoring these pathways, before and during treatment, provides a novel efficacious manner to gauge the degree of dsRNA replacement therapy required an individual patient or specific disease basis.

This invention provides a diagnostic procedure for determining a dsRNA deficiency state in a patient's sample, quantifying this deficiency (if any), and providing a therapeutic procedure for restoring any dsRNA deficiency identified by the administration of exogenous dsRNA optionally in combination with a lymphokine. Typically, a dsRNA deficiency state is evidenced within a component cell of the immune system whether or not the component cell is in the process of multiplication or differentiation. DsRNA deficiency is evidenced, for example, by the inability of a component cell of the immune system to maintain a sufficient level of bioactive RNase L. Monitoring of the intracellular dsRNA-dependent pathways before, during and after therapy enables the clinician to guage the degree of dsRNA replacement therapy required on an individual basis. Other means to assess dsRNA deficiencies are given in the detailed description that follows. "Mediators" are herein operationally defined as any intracellular moieties (e.g., specific oligonucleotides, proteins, dsRNAs—alone or in combination) which effect specific biochemical functions initiated by presence of dsRNA. Such biochemical functions will contribute to a strengthening of host defense mechanism(s) at either the single cell or whole (organism) level.

Conditions susceptible to the therapeutic procedures of this invention are generally those in which a deficiency of the intracellular dsRNA level is below normal limits, as compared with healthy individuals, dsRNA deficiency causing tissue pathology and/or in the presence of an abnormally low dsRNA level coupled with or coexisting with the presence of an intracellular pathogen. More specific conditions or tissue pathologies and constitutional symptoms include viral infections such as retrovirus infections including HIV, herpes family virus, paranyxovirus, rhinovirus, hepatitis and chronic fatigue syndrome. Others include uncontrolled proliferation of cancer cells and pathologies of the immune system whether or not the component cell is in the process of multiplication or differentiation.

By "mismatched dsRNAs" are meant those in which hydrogen bonding (base stacking) between the counterpart strand is relatively intact, i.e., is interrupted on average less than one base pair in every 29 consecutive base residues. Mismatching is an interruption of the normal geometry of the RNA double helix by in-pouching (or out-pouching) of the strands which represent points of vulnerability of the dsRNA to digestion by ribonucleases. The term "mismatched dsRNA" should be understood accordingly.

The dsRNA may be a complex of polyinosinate and a polycytidylate containing a proportion of uracil bases or guanidine bases, e.g., from 1 in 5 to 1 in 30 such bases (poly I. poly ($C_{4-29}$x>U or G).

The dsRNA may be of the general formula $rI_n \cdot r(C_{12}U)_n$. Other suitable examples of dsRNA are discussed below.

In the preferred mismatched dsRNA, $rI_n \cdot r(C_{12},U)_n$, a region consisting of an uninterrupted stretch of 6 to 12 base pairs, i.e., one-half to one full turn of an RNA helix, serves both as biotrigger causing release of lymphokines and as an obligate intracellular co-factor for enzymes comprising the natural antiviral pathways. The mismatched regions consisting of uracil residues is periodically inserted in the polypyrimidine strand to accelerate dsRNA hydrolysis and thus prevent toxicity.

The mismatched dsRNAs preferred for use in the present invention are based on copolynucleotides selected from poly ($C_n$,G) in which n is an integer having a value of from 4 to 29, and are mismatched analogs of complexes of polyriboinosinic and polyribocytydilic acids, formed by modifying $rI_n \cdot rC_n$ to incorporate unpaired bases (uracil or guanidine) along the polyribocytydylate ($rC_n$) strand. Alternatively, the dsRNA may be derived from poly (I). poly (C) dsRNA by modifying the ribosyl backbone of polyriboinosinic acid ($rI_n$) e.g., by including 2'-O-methyl ribosyl residues. These mismatched analogs of $rI_n \cdot rC_n$, preferred ones of which are of the general formula $rI_n \cdot r(C_{11-14},U)_n$ and $rI_n \cdot r(C_{29},G)_n$, are described by Carter and Ts'o in U.S. Pat. Nos. 4,130,641 and 4,024,222 the disclosures of which are hereby incorporated by reference. The dsRNAs described therin generally are suitable for use according to the present invention. In certain instances, complementary oligonucleotide duplexes (helices) will also suffice as replacement therapy.

Other examples of mismatched dsRNA for use in the invention include:

poly (I).poly ($C_4$,U)
poly (I).poly ($C_7$,U)
poly (I).poly ($C_{13}$,U)
poly (I).poly ($C_{22}$,U)
poly (I).poly ($C_{20}$,G)
poly (I).poly ($C_{29}$,G) and
poly (I).poly ($C_p$) 23 G>p dsRNA-Lymphokine Synergy. Since dsRNA exerts a significant component of its biological action through a specific lymphonine system mediated in part by IFN, I reasoned that it must (a) induce IFN in IFN-deficient cells as well as (b) activate relevant dsRNA-dependent enzyme mediators, the cellular dsRNA being non-inducible in cells failing to respond to exogenously applied IFN.

If dsRNA operates solely thought the IFN system and if dsRNA is in excess in cells, then an excess of IFN alone would exert as much bioactivity as the combinations of IFN and dsRNA. However, this must be a relatively rare condition since I have now found many examples of dsRNA-IFN synergy and a paucity of examples of no synergy. For example, I found that dsRNA was synergistic with human IFN alpha, beta or gamma in inhibiting the growth of cells form human bladder carcinoma, lung carcinoma, and fibrosacrcoma. I extended these results to 15 other human tumor cell lines with only one line failing to show antiproliferative synergy. I observed similar antitumor synergism was seen in some human tumor engrafted in nude mice and, clinically, I consistently observed that the combination of IFN and dsRNA was superior to either agent alone as an anticancer regimen in both kidney tumors and CML.

possible kinds of defects in dsRNA-mediated pathways which can be reversed by exogenously supplied dsRNA.

Figure 1:
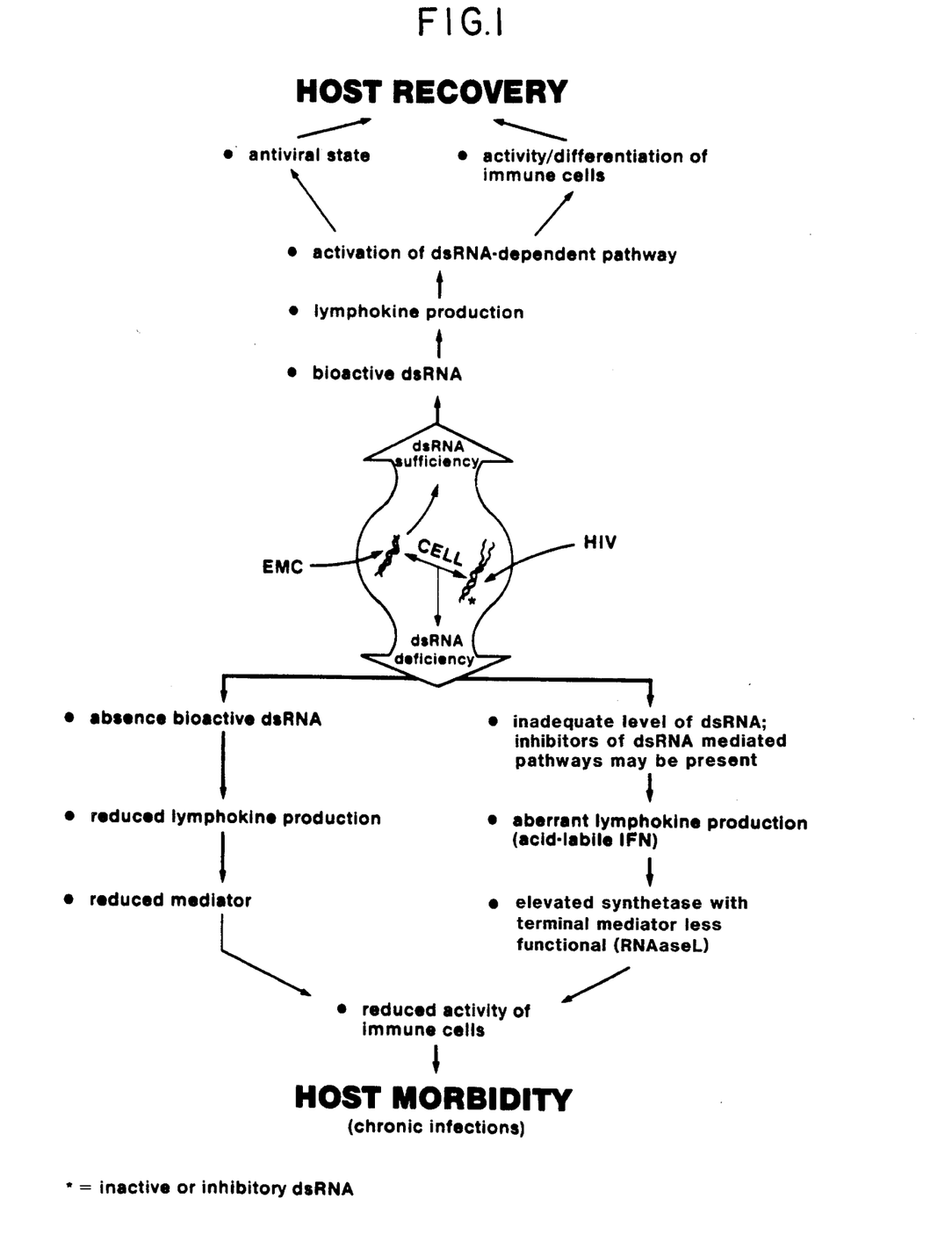
FIG. 1 is a flow chart illustrating the dual pathways to host morbidity and the pathway to host recovery.

The flow chart of FIG. 1 further illustrates the relationship between dsRNA sufficiency, leading to host recovery, and dsRNA deficiency, leading to host morbidity. Bioactive dsRNA is produced intracellularly or is introduced by certain events which lead to an antiviral state as well as immune cell differentiation and host recovery.

The in vitro measurement of 2-5A synthetase is of limited value, since this assay does not reflect the in vivo activity of the 2-5A synthetase. Therefore, I have developed a method to extract and quantitate the 2-5A from the peripheral blood mononuclear cells (PBMC) of healthy individuals and from pathogen-infected patients before and after mismatched dsRNA therapy. The concentration of 2-5A can be determined by the ability of the 2-5A to activity affinity-purified RNase L to degrade poly(U)[$^{32}$P]pCp.

TABLE 1

Intracellular 2-5A Concentration and In Vitro Activity of 2-5A Synthetase and RNase L in PBMC Extracts of Viral-Infected Individuals

| PBMA source | Weeks on mismatched dsRNA | 2-5A synthetase activity[a] | Intracellular 2-5A[b] | RNase L latent[c,d] | RNase L activated[d] |
|---|---|---|---|---|---|
| column | | 1 | 2 | 3 | 4 | 5 |
| #1 AIDS | 0 | 49 | <0.2 | 260 | — | — |
| + | 4 | 105 | ND | | | — |
| KS | 9 | 4 | <0.2 | | | — |
| | 15 | 10 | 1.8 | | | ++ |
| | 19 | 21 | 0.8 | | | — |
| | 24 | 26 | >10.0 | | | ++++ |
| | 28 | 20 | >10.0 | | | ++++ |
| #2 AIDS | −1 | 205 | <0.2 | 240 | — | — |
| + | 0 | 180 | ND | | — | — |
| KS | 4 | 117 | 1.4 | | | + |
| + | 8 | 19 | 2.4 | | | +++ |
| PCP | 21 | ND | 6.8 | | | ++ |
| | 26 | 9 | 5.4 | | | ++++ |
| #3 ARC | −6 | 11 | <0.2 | 270 | — | — |
| | 2 | 13 | ND | | | — |
| | 4 | 19 | <0.2 | | | — |
| | 17 | 3 | 1.8 | | | ++++ |
| #4 ARC | 0 | 130 | <0.2 | 270 | — | — |
| | 2 | 185 | ND | | | — |
| | 4 | 18 | 0.4 | | | + |
| | 8 | ND | <0.2 | | | — |
| | 22 | ND | >10.0 | | | ++++ |
| #5 LAS | 0 | 30 | 0.6 | 280 | — | — |
| 4 | 36 | <0.2 | | | — | |
| | 9 | 12 | 1.0 | | | ++ |
| | 17 | 21 | 3.0 | | | +++ |
| Healthy Volunteers | | 5 | 0.3–1.1 | 1350 | | ++++ |

[a] nmole ATP incorporated into 2-5A/mg protein as determined in poly(I):poly(C)-agarose assays; standard deviation 9%; ND, not determined.
[b] nmole/g protein as determined in core-cellulose assays (in duplicate); standard deviation 20%.
[c] dpm/50 µg protein as determined in radiobinding assays (in duplicate) (column 3); standard deviation 20%.
[d] determined in rRNA cleavage assays (columns 4 and 5) in two independent assays. Specific cleavage product (SCP) formation was quantitated by densitometric tracings of photographs of gels and is expressed as a ratio of SCP formation divided by 18S and 28S rRNA × 100; —, 0; +, 10–30; ++, 31–63; 64–85; ++++, 86–100.

dsRNA Deficiency States. As a prototype pathway, the 2-5A synthetase/RNase L pathway includes one or more dsRNAs, 2-5A, linked enzymes and inhibitors. There exists a direct biochemical connection between dsRNA and RNase L in that 2-5A, the product of dsRNA-dependent 2-5A synthetase, is a necessary cofactor for RNase L activity. The examples below are intended to exemplify a few of many Methods. Heparinized peripheral blood was obtained from ten healthy individuals and from five homosexual male patients with LAS, ARC and AIDS (as defined by the Centers for Disease Control). Clinical, virological and immunological features of patients involved in this study (patients #1–5) were characterized previously as patients 10, 8, 1, 7 and 2, respectively in my Lancet Jun. 6, 1987 article. PBMC were isolated on Ficoll-Hypaque. L929 and HL929

(an RNase L-deficient subclone of L929) cells were maintained in monolayer culture. Cytoplasmic extracts from L929 and HL929 cells were prepared in glycerol buffer and PBMC extracts were prepared in NP40 lysis buffer. Protein concentration of the extracts ranged from 10–15 µg/µl. KS, Kaposi's sarcoma; PCP, *Pneumocystis carnii* pneumonia.

Activity of 2-5A synthetase (column 1) was determined in PBMC extracts (50 µg protein/assay) using poly(I):poly(C)-agarose. 2-5A was isolated from the ethanol-soluble fraction of PBMC extracts (100 µg protein) ethanol, v/v). The ethanol-extracted 2-5A was then lyophilized and redissolved in water (20 µl). Concentrations of intracellular 2-5A present in PBMC extracts (column 2) were determined in core-cellulose assays with L929 cell extracts as the source of RNase L from calibration curves obtained with authentic 2-5A. Activation of RNase L by 2-5A in this assay is based on the conversion of poly(U)[$^{32}$P]pCp to acid-soluble fragments. In control experiments (in the absence of 2-5A), 6500 dpm was retained on glass fiber filters from a total of 17700 dpm of poly(U)[$^{32}$P]pCp added (1.3 µCi/nmole). In the presence of $\leq 1 \times 10^{-10}$ M authentic 2-5A, poly(U)[$^{32}$P]pCp was degraded 0%; in the presence of $>1 \times 10$ authentic 2-5A, poly(U)[$^{32}$P]pCp was degraded 100%. Latent RNase L levels were measured by two methods: (i) in radiobinding assays after the addition of 20,000 dpm of $p_3A_4$[$^{32}$P]pCp to PBMC extracts (50 µg protein/assay) (column 3) and (ii) in ribosomal RNA cleavage assays in the presence of 2-5A (column 4). Extracts (150 µg protein/assay) prepared from L929 cells were incubated in the presence of 5 µl of ethanol-soluble fractions of PBMC extracts and $1 \times 10^{-8}$ M $p_3A_3$ in a final volume of 20 µl for 60 minutes at 30° C. The total RNA was extracted, denatured and analyzed by electrophoresis on 1.8% agarose gels. The ethidium bromide stained RNA bands were visualized under UV light. Activated RNase L levels (column 5) were determined by ribosomal cleavage assays in the absence of added 2-5A.

The concentration of functional 2-5A in PBMC extracts varied from 0.3 to 1.1 nmole/g protein for healthy humans and from below detectable levels to 0.6 nmole/g protein in PBMC extracts from virus-infected patients before mismatched dsRNA treatment (Table 1, column 2). However, 2-5A accumulated to greater than 10.0 nmole/g protein as mismatched dsRNA therapy progressed. 2-5A activated, partially-purified RNase L has been previously reported to preferentially cleave polu(U), but not poly(C). The isolated human 2-5A, like authentic 2-5A, could activate affinity-purified RNase L from either L929 cells or from PBMC of healthy humans to specifically degrade poly(U); see Table 4. It is important to note that when TCA is used to extract 2-5A from PBMC, a poly(C) degrading activity was extracted in addition to the poly(U) degrading (RNase L) activity. This poly(C) degrading TCA-extractable activity could be eliminated by protease digestion or further ethanol extraction. The poly(C) degradative activity was found in TCA-soluble fractions of PBMC from all humans, but in none of the permanent cell lines (i.e., HeLa L929, HL929) tested thus far. The poly(C) degrading activity was not detectable in any of the ethanol-soluble fractions of PBMC.

TABLE 3

Effect of dsRNA on Infectious Center Formation by Respiratory Syncitial Virus-Infected CCL 25 Cells

| Concentration of mismatched dsRNA[a] | Infectious Centers[b] Plate Counts | Mean Counts | Percent Reduction |
|---|---|---|---|
| 0 µg/ml | 49, 44, 15*, 33 | 42.0 | |
| 0.5 µg/ml | 38, 36, 26, 16* | 33.3 | 21.7 |
| 1.0 µg/ml | 54, 44, 42, 53 | 48.5 | 15.5 |
| 2.5 µg/ml | 37, 32, 24, 30 | 30.8 | 26.7 |
| 5.0 µ/ml | 27, 14, 17, 18 | 19.0 | 54.8 |
| 10.0 µg/ml | 1, 1, 7, 5 | 3.5 | 91.7 |
| 25.0 µg/ml | 0, 2, 0, 0 | 0.5 | 98.8 |

*Data not used to calculated mean counts.

The highest concentration of mismatched dsRNA [rI.r($C_{12}$, U)$_n$, 25 µg/ml] was non-toxic to CCL 25 cells.
(a) Quadruplicate wells of confluent CCL 25 cells in 24 well plates were re-fed with 1.5 ml maintenance medium containing dsRNA at concentrations indicated above 1 hour prior to plating of RSV-infected cells. Mock-treated cells were re-fed dsRNA-free maintenance medium.
(b) $4 \times 10^4$ CCL 25 cells in suspension were infected in a total volume of 1 ml containing $5 \times 10^5$ PFU of RSV (MOI=12). Viral adsorption occurred during a 2 hour incubation at 37° C. with intermittent resuspension of the cells. At the end of this period, the suspension was diluted 1/100 in maintenance medium. 0.5 ml aliquots of the infected cell suspension were added directly to each experimental well, and to each infectious center-control well. 0.5 ml volumes of maintenance medium were added to cell control wells. All cultures were incubated at 37° C. in 5% $CO_2$-95% air for 72 hours, fixed with methanol and stained with Giemsa. Plaques (Infectious Centers) were counted microscopically.
moi refers to multiplicity of infection; that is, the approximate number of viral particles available to infect each target cell. PFU refers to plaque forming units; that is, the number of viral units as determined by counting the cytopathic (dead cells).

Although there have been reports on the presence of 2-5A in tissues isolated from untreated animals as well as the accumulation of 2-5A in tissues from mice treated with dsRNA, mine is the first report of the accumulation of 2-5A in a human tissue. It is well established that authentic 2-5A binds to and activates RNase L to degrade rRNA to highly characteristic specific cleavage products (SCP). Therefore, I characterized the activity of the 2-5A isolated from PBMC extracts in rRNA cleavage assays. The specific cleavage pattern generated by RNase L with ethanol-extracted 2-5A was the same as that obtained in the presence of authentic 2-5A. These results show that i.v. administration of mismatched dsRNA to virus-infected patients caused dramatic increases of 2-5A in blood cells beginning from concentrations which were below detection.

RNase L Activity

The absence of RNase L activity in HIV-infected individuals was confirmed and extended (Table 1, columns 3, 4, 5). A sensitive technique based on the cleavage specificity of 2-5A activated RNase L on rRNA (Wreschner et al, *Nucleic Acids Res.*, vol. 9, pp. 1571–1581, 1981) permitted the measurement of activated RNase L in extracts of PBMC isolated from as little as one ml of peripheral blood. Extracts of an RNase L-deficient subclone of the L929 cell line (HL929) were utilized as the source of ribosomes. PBMC extracts of HIV-infected patients had 5–7 times lower levels of latent RNase L than those of healthy individuals as determined in radiobinding assays (Table 1, column 3;

240–280 dpm vs. 1350 dpm). Similar observations have been reported by Wu et al (*AIDS Research*, vol. 2, pp. 127–131, 1986). The application of the radiobinding assay is limited with respect to the determination of latent RNase L level in patients treated with mismatched dsRNA because accumulated 2-5A present in PBMC samples from these patients (Table 1, column 2) can compete for binding to RNase L. Therefore, determination of the level of the 2-5A-activated RNase L was essential.

First, levels of activated RNase L were determined by measuring the specific cleavage of rRNA by PBMC extracts in the absence of exogenously added 2-5A (Table 1, column 5). Using this assay, I demonstrated that RNase L was not activated in PBMC extracts of HIV-infected patients before therapy (polyacrylamide gels shown in FIG. 3). Knowing that the levels of intracellular 2-5A were low in these PBMC samples (Table 3, column 2), this result was not unexpected. However, extracts of PBMC from all healthy individuals tested showed the presence of activated RNase L which produced specific cleavage products in rRNA cleavage assays, even though 2-5A in some healthy individuals was as low as 0.3 nmole/g protein (Table 3, column 5). It is significant that the absence of RNase L activity in samples from HIV-infected patients before therapy cannot be due to accumulation of a competitive inhibitor of 2-5A as reported (Caylet et al *European J. Bioch.*, vol. 143, pp. 165–177, 1984) RNase L activity could not be restored by the addition of authentic 2-5A (Table 1, column 4).

Next, levels of latent RNase L were determined by two independent measures. Latent RNase L activity was determined in the rRNA specific cleavage assay, but in the presence of added 2-5A (Table 3, column 4). In samples taken before mismatched dsRNA therapy, no latent RNase L activity could be detected in any of the 5 patients examined.

The technique of photoaffinity labeling with $p_3A_4[^{32}P]pCp$ was used to determine further if RNase L was missing or altered in PBMC of HIV-infected patients. Previous photoaffinity labeling studies have identified a protein of $M_r 80,000$ with binding affinity for $p_3A_4[^{32}P]pCp$ and specific poly(U) endoribonucleolytic activity as RNase L. Affinity labeling of RNase L present in PBMC extracts was determined using $p_3A_4[^{32}P]pCp$. RNase L from PBMC extracts (50 μg protein) from a normal individual was compared with an ARC patient (patient before mismatched dsRNA therapy) or L929 cell extracts (50 μg protein) was photolabeled after the addition of $p_3A_4[^{32}P]pCp$ (30,000 dpm, 3000 Ci/mmole) in the absence or the presence of authentic $p_3A_4$ ($1\times10^{-8}$ M). RNase L from PBMC extracts from a normal individual (100 μg protein) was purified on 2-5A core-cellulose and photolabeled after the addition of $p_3A_4$ [$^{32}P$]pCp (30,000 dpm; 3000 Ci/mmole). After incubation at 0° C. for 90 minutes, the samples were transferred to ice-cold porcelain spot plates and photolysed for 3 minutes, using 254 nm UVG-11 Mineralight lamp (Ultraviolet Products) at a distance of 2 cm (1.0 J/m²). The positions of the protein markers and the $M_r 80,000$ RNase L were determined.

My photolabeling studies revealed that $p_3A_4[^{32}P]pCp$ was covalently linked to a protein with an $M_r$ of 80,000 in extracts of PBMC from healthy humans (polyacrylamide gel data not shown). However, no protein was labeled in extracts of PBMC from a chronically virally-infected patient. Under identical experimental conditions, a protein of $M_r$ 80,000 was specifically photolabeled in L929 cell extracts. Addition of $p_3A_4$ ($1\times10^{-8}$ M) to incubation mixtures containing the $p_3A_4[^{32}P]pCp$ prevented photolabeling thus providing me additional evidence that the photolabeling was highly specific for RNase L. Photolabeling studies with the protein purified from PBMC extracts from a healthy human by the core-cellulose method revealed covalent linkage to a protein of $M_r 80,000$, which was capable of degrading poly(U), but not poly(A), poly(C) nor poly(G), in the presence of authentic 2-4A (Table 4). Taken together, these results confirm that the protein purified from PBMC of healthy individuals and photolabeled by $p_3A_4[^{32}P]pCp$.

After 4 to 17 weeks on mismatched dsRNA therapy, activated RNase L was first detected in PBMC extracts from all five chronically infected patients; by 17 to 28 weeks of mismatched dsRNA therapy, activated RNase L activity for all five patients was equivalent to RNase L levels observed in healthy individuals (Table 1, column 5). The level of activated RNase L showed very close correlation with the concentration of functional 2-5A isolated from the same samples (Table 1, as compared with columns 2 and 5). Of utmost interest, patient 1 maintained an elevated intracellular 2-5A level and fully activated RNase L at 28 weeks, 3 weeks after mismatched dsRNA therapy was discontinued (Table 1, columns 2 and 5).

The experiments described here show that five HIV-infected patients possess a common molecular phenotype in blood mononuclear cells: reduced levels of 2-5A and absence of detectable RNase L activity. Blood mononuclear levels for healthy individuals exhibited a different phenotype in that 2-5A levels were higher, on average, and RNase L activity was readily detectable. The latter phenotype is more consistent with that expected of a functional 2-5A synthetase/RNase L pathway. In normal individuals, the steady state pool of 2-5A is detectable; an appreciable fraction of this intracellular 2-5A may become tightly associated with RNase L, thereby activating the RNase L. In the experimental procedures elucidated herein, it is clearly established that in blood mononuclear cells of chronic virally-infected persons, the intracellular levels of 2-5A are below detection and there is no activated RNase L as determined by presently available technology.

In summary, an important discovery here was that defects in the 2-5A synthetase/RNase L pathway were reversed by therapy with mismatched dsRNA. My results are not explained simply by normal levels of RNase L protein without 2-5A, since RNase L activity in vitro was not restored by adding 2-5A to PBMC extracts. RNase L protein must be absent or inhibited, a conclusion confirmed by lack of binding by a photoaffinity-labeled analog of 2-5A. In the treated patients described here, HIV RNA levels in PBMC were reduced within 10–20 days and the number of infections centers (co-cultivation) of HIV-infected PBMC declined more slowly. The increase in intracellular 2-5A and RNase L activity determined here more closely parallel the loss of infectious centers in these patients. My results clearly show that the 2-5A synthetase/RNase L pathway became more active in treated HIV-infected patients than in healthy humans after several weeks of therapy with mismatched dsRNA. My results are thus fully consistent with the hypothesis that certain chronic viral infections represent a dsRNA deficiency state which can be reversed by supplying exogenous source of bioactive dsRNA.

The invention is further described with reference to the following illustrative examples in which all parts and percentages are by weight unless otherwise indicated.

EXAMPLE 1 - Coordinated IFN and dsRNA Treatments

Figure 2:
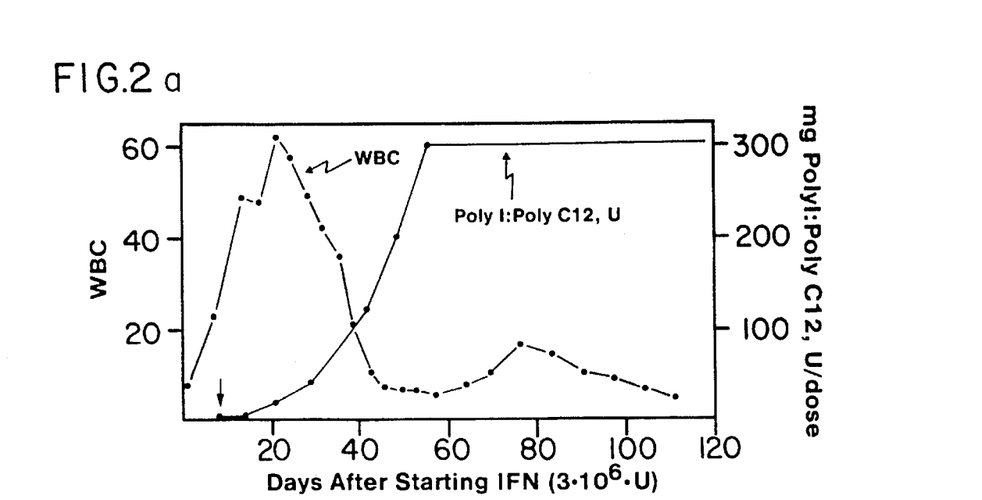
FIG. 2A is a graph plotting the number of days prior to and after initiation of IFN therapy in the amount indicated against synthetase activity.
FIG. 2B is a graph comparing white blood cell count and quantity of mismatched dsRNA after 120 days of treatment.
Figure 3A:
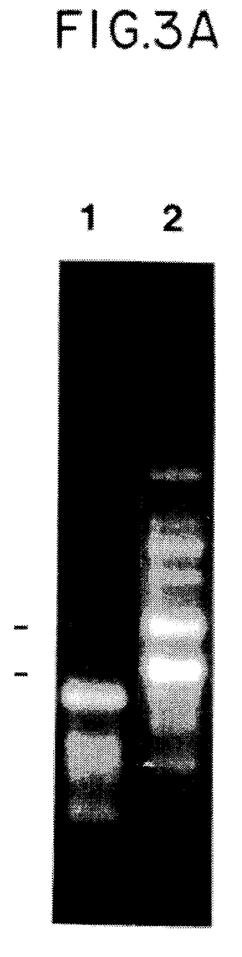

A dsRNA-deficiency state is one in which IFN-treated tumor cells show little or no IFN-induced growth arrest. This is a functional or operational test of dsRNA deficiency which can be confirmed rigorously if need be by various biochemical measurements described below. In many instances, a clinical diagnosis of a "dsRNA deficiency" will become sufficient as my invention becomes more widely practiced. IFN$^r$ tumor cells are known to be rarely deficient in IFN receptors and may contain high or low levels of mediators, but in either case I find that they respond to exogenously supplied dsRNA. These examples are of clinical relevance since they indicate that dsRNA will consistently expand the therapeutic range of IFN in particular and also other lymphokines as well, e.g., IL-2, various colony stimulating factors and TNF. Chronic myelogenous leukemia (CML) is a case in point. About 60% of CML patients respond to IFN alone, while 40% do not. The latter fail to induce 2-5A synthetase in blood mononuclear cells (MNC) as described by Rosenblum et al. in *Cancer Res.*, vol. 46, p. 4848, (1986). FIG. 2-A presents an IFN-resistant case which I treated with mismatched dsRNA plus IFN following a short course (7 days) of IFN alone then with mismatched RNA in combination with IFN. This patient failed to induce 2-5A synthetase activity while receiving IFN alone but did show a substantial increase in activity of this mediator with the combination of IFN and mismatched dsRNA. Induction of 2-5A synthetase was accompanied by complete hematologic remission which has lasted for several months, after a transient increase in blood cell number caused by interrupting prior chemotherapy. The activity of RNase L was also measured and found to be 10 to 100-fold higher than normal (FIG. 3A, lane 1) yielding RNA cleavage products in vitro which represented further degradation beyond the usual rRNA cleavage products of normal RNase L. RNase L activity returned to normal levels and cleavage profiles after 30 days of therapy with the IFN/dsRNA combination (FIG. 3A, lane 2). I note here that this kind of response was observed regularly.

EXAMPLE 2 - Viral Infection of T4 Cells

Another dsRNA-deficiency state is one where the animal virus itself (or its replicative intermediates) supply an inhibiting dsRNA or a partly bioactive dsRNA for mediator activations, even though IFN and its mediators are induced by virus infections. Many viruses associated with chronic symptomatology in the host will fall in this category. Infection of T4 cells by HIV can also constitute such a situation as suggested by FIG. 1. HIV replication in T4 cells was effectively blocked by mismatched dsRNA in tissue culture (see my published European patent application No. 0,213,921) despite the fact that HIV replication in these same cells was only moderately suppressed by IFN alpha, beta or gamma, alone or in physiological mixtures. Since HIV RNA itself displays considerable secondary structure which does not block its own expression, different dsRNAs probably elicit different biological responses. One region of extensive dsRNA structure at the 5' end of HIV mRNA binds an Mr 15000 polypeptide suspected to be the HIV transacting (tat) protein (Muesing et al., *Cell*, vol. 48, p. 691, 1987) and I suggest that mismatched dsRNA may compete with HIV RNA for tat protein. The property of supporting efficient HIV infection, as well as other chronic viremias, may be a second dsRNA deficiency state in ARC and AIDS.

EXAMPLE 3 - HIV Infected Cells

A third kind of dsRNA deficiency state is observed in blood lymphocytes of individuals with chronic viral infections such as HIV in ARC and AIDS. Preble et al. (*J. Infect. Dis.*, vol. 152, 1985) reported that these cells possess elevated levels of dsRNA-dependent 2-5A synthetase, a finding I confirmed. This result was typical of a series of consecutive ARC and AIDS patients which I studied and helped form the basis for my invention in respect of the central role of dsRNA in host recovery and the necessity to replace dsRNA deficiency conditions by an appropriate source of exogenous dsRNA.

I reported RNase L to be often depleted in ARC and AIDS patients (Jun. 6, 1987, *The Lancet*); however, I reported that RNase L can return to more normal activity after several weeks of therapy with mismatched dsRNA in certain cases. As FIG. 3B, lane 4 suggests, ARC lymphocyte extracts can inhibit the activity of normal RNase L under certain conditions. Since tricholoacetic acid (TCA) and ethanol-soluble extracts lacked inhibiting activity, the transferable inhibitor observed in ARC patient's MNC cannot be that described by Williams et al in herpes-infected cells (*Virology*, vol. 151, p. 233, 1986). Also, I consistently saw no inhibitor in MNC extracts from healthy individuals (Lane 5) studied to date.

Since mismatched dsRNA acts directly on these cells, they must also be dsRNA-deficient. Thus, I have shown that different dsRNAs have different bioactivities (the HIV dsRNA being inhibitory whereas mismatched dsRNA is not). It appears that lymphocytes from ARC and AIDS patients are dsRNA-deficient in the sense that only some of the necessary dsRNA-dependent functions are carried out. One function at least, the maintenance of sufficient levels of bioactive RNase L, is not carried out unless exogenous dsRNA is added.

EXAMPLE 4 - Chronic Fatigue Syndrome

An example of dsRNA deficiency requiring appropriate replacement therapy is Chronic Fatigue Syndrome (CFS), a condition involving some 10 to 12 million Americans, a difficult to diagnose, ubiquitous disorder characterized by extreme fatigue, lymph gland enlargement and constitutional symptoms such as weight loss, loss of appetite and the like. The condition occurs primarily in young, active people. While some CFS patients manifest neuropsychiatric changes such as depression, loss of memory and similar derangements, chronic fatigue syndrome is sometimes difficult to distinguish from entirely neurological disorders, particularly depression. Various laboratory studies indicate that many different viruses may replicate in individuals having Chronic Fatigue Syndrome, and that these individuals become, in effect, "virus sewers". Viruses such as Epstein-Barr, cytomegalovirus, retroviruses, herpes viruses, etc., are often present in such individuals.

The in vivo concentration of 2'-5'A molecules, a biochemically related, accurate measurement of intracellular dsRNa levels, in normal individuals and subjects with Chronic Fatigue Syndrome, is assessed as follows: Ethanol-soluble fractions of patient samples (Ficoll-Hypaque-purified peripheral blood lymphocytes) were analyzed for their 2'-5'A content in 2'-5'A core-cellulose assays (affinity chrmoatography (with poly U-{$^{32}$P}-pCp. In this assay, the ability of 2'-5'A-activated RNase L to hydrolyze poly(U) is used to determine the concentration of functional 2'-5'A.

Reference values were established by testing 15 normal subjects with no recent history of viral infections as evidenced by lack of fever, absence of constitutional symptoms, rashes, etc. Concentrations of their lymphocyte 2'-5'A levels were determined using calibration curves obtained with authentic 2'-5'A molecules. Normal individual reference values, expresses as nanomoles of 2'-5'A within a range of 0.3 to 1.1 nanamole per gram of PBMC cells.

Using this assay method, ten patients exhibiting the usual symptoms of Chronic Fatigue Syndrome were tested and the results obtained were as follows:

TABLE 2

| Subject Number | n moles 2'-5' A per gram lymphocyte protein |
|---|---|
| 1 | <0.8 |
| 2 | <0.05 |
| 3 | <0.05 |
| 4 | <0.05 |
| 5 | nd* |
| 6 | nd* |
| 7 | <0.01 |
| 8 | <0.01 |
| 9 | <0.01 |
| 10 | <0.08 |

*not detectable

Patients with Chronic Fatigue Syndrome have generally below 0.1 and always below about 0.2 n moles of 2'-5'A per gram of lymphocyte protein. Definitive treatment of such individuals with Chronic Fatigue Syndrome is provided by supplying exogenous dsRNAs, as required, until the intracellular level of 2'-5'A oligonucleotides reaches normal indicating the return of the intracellular dsRNA level to normalcy and/or the patient's clinical symptomology abates. The patient's resistance to Chronic Fatigue Syndrome and opportunistic viruses is maintained by continuing to measure the patient's intracellular 2'-5'A oligonucleotide levels and supplying exogenous dsRNA, as required, to maintain the 2'-5'A level in the normal range, usually in excess of 0.2 nanamoles of 2'-5'A per gram of lymphocyte protein.

The natural dsRNAs play a role in host defense when challenged with a viral disease such as Chronic Fatigue Syndrome. Specific reduction in bioactive dsRNA, or enzymes which depend on dsRNA, notably a viral-associated inhibitor of RNase L coupled with abnormally low levels of 2'-5'A in peripheral blood lymphocytes, within specific cells contributes to disease progression. dsRNA, notably mismatched dsRNAs, reverse disease progression.

Patients having Chronic Fatigue Syndrome are treated with intravenous infusions of 200 to 600 mg (depending upon disease severity and viral burden, etc.) of $rI.r(C_{11-14},U)$ twice weekly and 1-'5'A levels increase in association with clinical improvement. The amount of dsRNA administered and the frequency of administration will be guided by the 2'-5'A levels measured in conjunction with the patient's clinical improvement. Amounts of dsRNA administered will provide a level of from 0.01 to 1,000 micrograms of dsRNA per milliliter of the patient's systemic blood circulation immediately following administration measured at a point distal from the point of infusion.

EXAMPLE 5 - Antiviral Effect on T4 Cell Populations dsRNA, particularly mismatched dsRNAs, exogenously administered restore a viral-infected patient's ability to respond to viral challenge. As an illustration of a viral condition, HIV was selected as one of the most damaging. The primary target of an HIV infection are the T4 lymphocytes and their population is dramatically reduced as the viral infection progresses. Further, T4 cell population decline is an unwelcomed, quantifiable disease parameter whose decline reflects a worsening of the disease. Conversely, an increase in the T4 cell population is a favorable diagnostic indication showing an improvement in therapeutic intervention.

Figure 4:
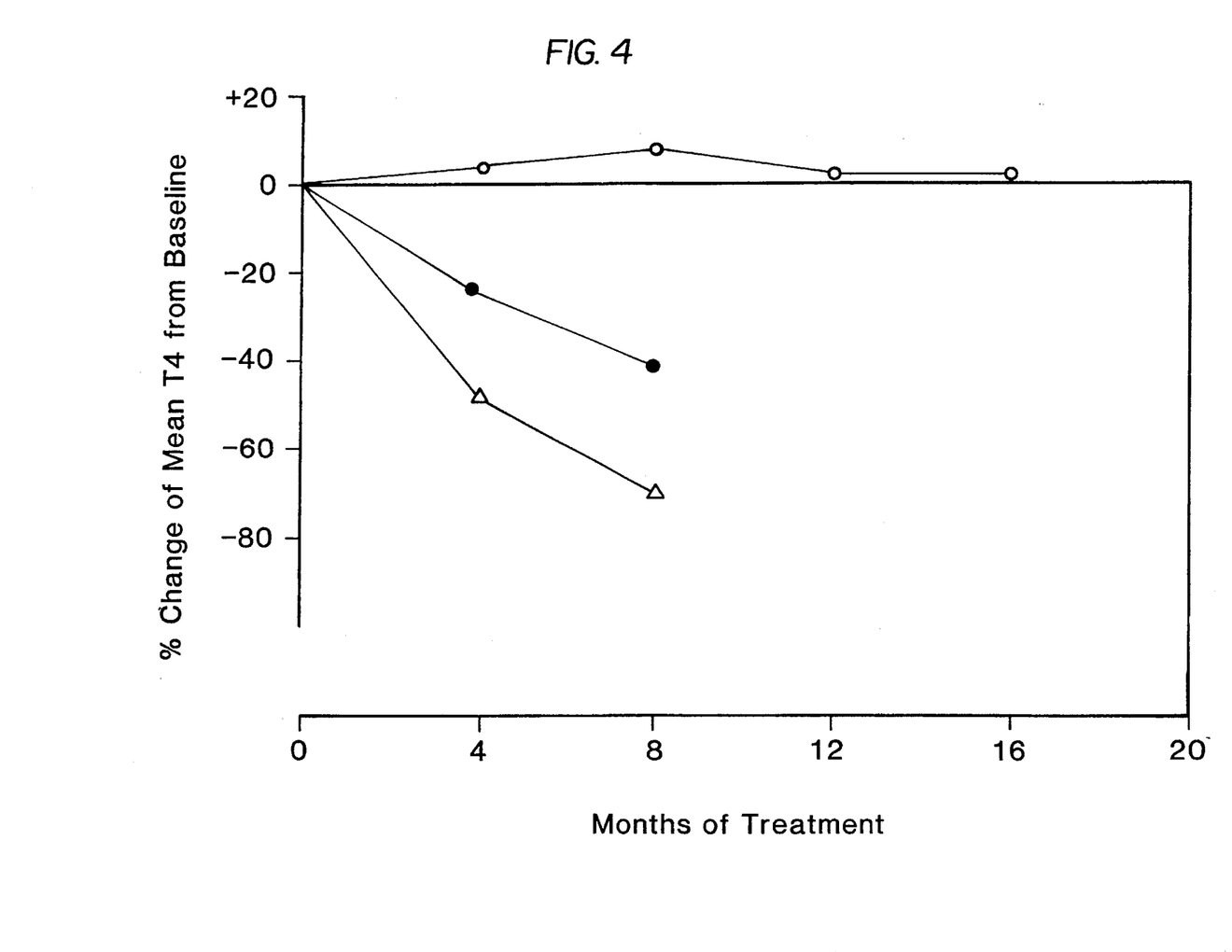
FIG. 4 is a graph comparing absolute number of T4 lymphocyte levels per cubic millimeter of blood, expressed as % change from baseline, to months of therapy.

The normal T4 cell population for a healthy individual is 400 cells per cubic millimeter of blood. Thirty-nine patients (see FIG. 4) diagnosed as being in the pre-ARC or ARC category were measured and divided into three categories based upon the absolute number of T4 cells per $mm^3$ of blood: (a) greater than 300 (18 patients, data not shown); (b) 150 to 300 (13 patients); and (c) less than 150 (8 patients, mean=92). The patients in groups (b) and (c) were treated with 100–200 mg $rI_n.(C_{12},U)$ (Ampligen®) twice weekly by IV infusion for 3 to 16 months (mean=8.4 months). For purposes of comparison, T4 cell population data from untreated HIV-infected patients (181) are included (connected deltas) to show the otherwise inevitable decline in the T4 population in such individuals.

The baseline is the initial absolute T4 lymphocyte concentration before initiating therapy. Improvement is expressed in terms of percent change, positive or negative, from this baseline as shown graphically in FIG. 4. Patients were initially observed and T4 cell concentration measured. The (b) group of patients, shown in FIG. 4 by which the open circle connected line, had T4 cell concentrations in the range of 150 to 300 cells/$mm^3$. These patients received initially 100 mg Ampligen (IV twice weekly) as a precautionary measure and observed for adverse reactions, then the dose was increased to 200 mg. given at the same frequency. A second group of patients (c) whose T4 cell concentration was less than 150 cells/$mm^3$ were given 300 mg Ampligen (IV, twice weekly). The percent change from baseline is shown in the line connecting the solid circles. Untreated patients (181), with absolute T4 lymphocyte continued with a sharp decline as shown in the line connecting the deltas.

Mean T4 cells increased 4.3% after 4 months in 30 patients, 8.0% after 8 months in 10 patients and 17% after 12 months in 6 patients. Only 2 patients (mean baseline T4=82 cells) advanced to AIDS while receiving continuous $rI_n.(C_{12},U)_n$ therapy and another ARC patient who discontinued therapy for 2 months developed Kaposi's sarcoma.

These data demonstrate that infected individuals whose absolute T4 lymphocyte levels are less than 150 cells/$mm^3$ require significant quantities of the drug to slow the rate of T4 cell reduction; however, patients in the 150–300 range are effectively maintained at lower dosage levels. These data also underscore the importance of initiating therapy before drastic decline in the HIV patient's condition.

These data further demonstrate the direct relationship between the magnitude of the dsRNA deficit (assessed indirectly but accurately by absolute T4 cell populations) and the quantity of exogenous dsRNA required to correct the deficiency and restore the patient towards full health (as a restoration of the T4 cell population to values approaching that in less severely infected and uninfected individuals)—the larger the T4 deficit, the greater the quantity of dsRNA required to restore the deficit.

EXAMPLE 6 - dsRNA Replacement Therapy in Paramyxovirus Infection

Another example of a transient dsRNA deficiency requiring appropriate replacement therapy may be various phases in neonatal life and infant development wherein the body's immune system is not fully developed. In these instances, potentially life-threatening infections may emerge from what would otherwise be self-limiting infections of adolescence or adulthood. A specific example follows: members of the paramyxovirus family such as respiratory syncytial virus (RSV) can cause acute bronchiolitis in infants (typically 6 to 18 months of age) with their yet-to-be fully developed immune intriasic antiviral defense systems. In such cases, I show below that replacement therapy with dsRNA $[rI_n.r(C_{12},U)_n]$ can be crucial and abort what otherwise may be a lethal event (death).

To develop this novel insight, I grew a human amnion-derived cell line designated CCL 25 under standard laboratory conditions. CCL 25 cells (obtained from the American Type Culture Collection, Rockville, Md., USA) support the growth and replication of RSV in a manner analogous to human neonatal bronchiole tissues. The attached table shows conclusively that I was able to reduce the multiplication of RSV by approximately 99% using doses of dsRNA which I have independently shown are well-tolerated in humans.

TABLE 4

Activity of 2-5A and RNase L Isolated from PBMC of Humans on Homopolyribonucleotides

| | Source of RNase L: | | | |
|---|---|---|---|---|
| | PBMS % Degradation[a] | | L929 cells % Degradationa[a] | |
| | Poly(U)-$[^{32}P]$pCp | Poly(C) $[^{32}P]$pCp | Poly(U)-$[^{32}P]$pCp | Poly(C)-$[^{32}P]$pCp |
| Authentic 2-5A | 84 | 0 | 93 | 0 |
| 2-5A Isolated from PBMC | 34 | 0 | 45 | 0 |

[a]average of 3 independent determinations; standard deviation 20%.

Methods. RNase L, purified from extracts (100 μg protein) of PBMC from a healthy individual or from L929 cells, were incubated under core-cellulose assay conditions in the presence of poly(U)$[^{32}P]$pCp (11000 dpm, 0.10 μCi/mmole) or poly(C)$[^{32}P]$pCp (12400 spm, 0.33 μCi/nmole) after the addition of authentic 2-5A ($p_3A_3$, $5\times10^{-7}$ M) or 2-5A isolated from an extract (12.5 μg protein) of PBMC from patient #5 (at 9 weeks of mismatched dsRNA therapy). The poly(U)$[^{32}P]$pCp and poly(C)$[^{32}P]$pCp were synthesized from poly(U) or poly(C) (Sigma) and $[^{32}P]$pCp (Amersham) by T4 ligase (Bethesda Research Laboratories). In control experiments (in the absence of $p_3A_3$) 3300 dpm of poly(U) $[^{32}P]$PCP and 11000 dpm of poly(C)$[^{32}P]$pCp were retained on glass fiber filters and are referred to as no (0%) degradation.

Since it is established that infectious center formation induced by RSV involves direct cell to cell spread of the virus, I have now established that simply by raising the intracellular concentration of dsRNA effectively I can reduce the cell to cell dissemination of RSV without significant untoward effects on other bodily tissues.

Thus, disease pathology caused by other potentially self-limited pathogens such as RSV (paramyxovirus family) as well as other RNA producing viruses which affect the nasal/tracheal/bronchial tree, such as rhinoviruses, or influenza viruses, may be effectively contained by a dsRNA replacement therapy mechanism. Local portals of pathogen entry, such as (but not limited to) the airways, may have intrinsically or transiently lower dsRNA content (dsRNA being herein operationally defined as any of those molecules which trigger the relevant immune/antiviral defense cascades to thwart pathogen reproduction/tissue-induced pathology).

EXAMPLE 7 - Treatment of Hepatitis

Numerous reviews of liver disease in patients with AIDS have appeared in the literature over the last 2–3 years. The recurrent theme is the wide array of histologic findings in both needle directed biopsy specimens and biopsy at time of autopsy. In all studies below mentioned the U.S. Center for Disease Control, Atlanta, Ga., USA, criteria for a diagnosis of AIDS was satisfied. Typical presenting symptoms and signs of patients found to have extensive hepatic disease are entirely nonspecific and include weight loss, fever, lymphadenopathy, hepatosplenomegaly, and abdominal pain. Serum transaminases typically are elevated in most AIDS patients. There is a propensity for elevated alkaline phosphatases to be disproportionately high; it has been suggested that such elevations of alkaline phosphatase are correlated with a histologic diagnosis of granulomatas disease. Autopsy studies done in unselected patients (i.e., unbiased patient selection as opposed to biopsy studies in patients with hepatomegaly and elevated liver function tests) universally demonstrate a wide array of intrahepatic pathology. Approximately 80–90% of all autopsy cases in AIDS patients demonstrate abnormal liver anatomy. Hepatic derangements include vascular congestion, portal inflammation, steatosis, focal necrosis, granulomata, bile stasis, cirrhosis and Kupffer cell hyperplasia (in approximate order of frequency). Of interest, the intraphepatic diagnosis of Kaposi Sarcoma at autopsy was the most common specific intrahepatic pathogen (18%) in one study (Schneiderman et al, *Annals Internal Med.*, Vol. 105, pg. 207, 1987).

Biliary disease has recently been described in a small number of AIDS patients. Isolated case reports have described sclerosing cholangitis, intrahepatic destructive bile duct lesions, and benign extrahepatic biliary obstruction in patients with AIDS. No specific etiologic agent has been documented in these cases; cytomegalovirus has been implicated as a possible cause secondary to histopathologic findings on biopsy. In AIDS patients with benign extrahepatic biliary obstruction, common presenting complaints have included liver, right upper quadrant pain and modest bilirubin elevations. At autopsy or laparatomy a diagnosis of ampulai of vater structure secondary to fibrosis was made. In at least two cases of extrahepatic obstruction, cryptosporidia were isolated from the biliary tree. Other cases were notable for cytomegalovirus inclusive bodies in the vicinity of the ampulae of vater. As with the above cases of intrahepatic cholangitis, specific etiology is unknown and the specific pathogens may have only a casual role in the pathogenesis of these disorders.

I determined that dsRNA infusion $[rI.r(C_{12},U)_n$, 200 mg, twice weekly, IV] also corrects or significantly ameliorates the underlying cellular abnormality associated with hepatitis B virus (HVB) multiplication. To accomplish this insight, the following method was used: Evaluation of Sera or Plasma for HBV-Specific DNA: The presence of serum (or plasma)-associated HBV DNA, an indicator of the presence of hepatitis B virus, was determined by slot-blot hybridization. Serum samples were diluted in $NH_4OAc$ to a final concentration of 1 M salt. Using a 72-wall microfiltration apparatus (Schleicher & Schuell, Keene, N.H.), the samples were applied directly to a nitrocellulose filter that had been presoaked for 10 minutes in 1 M $NH_4OAc$. The DNA was denatured in situ with alkali and then neutralized. Dilutions of purified HBV DNA in normal human serum were assayed in an identical manner to quantitate each slot-blot hybridization. The filters were baked, prehybridized, hybridized, and washed under conditions of high stringency, and autoradiographed using standard conditions (Maniatis, T., Fritsch, E. F. and Sambrook, J., Molecular Cloning: A Laboratory Manual, Cold Spring Harbor Laoratory, Cold Sprig Harbor, 1982). The HBV probe DNA used in the hybridizations was obtained from a recombinant plasmid containing a single, unit length copy of HBV DNA (HBsAG serotype adw2) cloned at the EcoR1 site. The plasmid was digested with EcoR1 and the HBV DNA was purified by 2 cycles of preparative agarose gel elecrophoresis and electroelution. The purified HBV DNA was labeled with $^{32}$P-dCTP to a specific activity of $1-2 \times 10^9$ cpm/µg using the random-prime labeling technique (Feinberg, A. P. and Vogelstein, B., *Analyt. Biochem.*, 132:6–13, 1983). The level of sensitivity obtained with this assay is 1 pg of HBV DNA. At this level of sensitivity, I am detecting $2.9 \times 10^5$ molecules of HBV DNA.

The autoradiographs produced were evaluated for degree of relative intensity and numerically ranked according to observed intensity and are reported in the following Table. Days of therapy are given parenthetically.

TABLE 4

Effect of dsRNA Administration on Reducing Concentration of HBV (hepatitis B virus) DNA in Bodily Fluid

| Sample Number | Patient #1 (day sampled) Blot Intensity P Therapy | Patient #2 (day sampled) Blot Intensity | Patient #3 (day sampled) Blot Intensity |
|---|---|---|---|
| T* | 3+ (0) | 3+ (0) | 3+ (0) |
| 1 | 3+ (20) | 3+ (21) | 3+ (31) |
| 2 | 3+ (64) | 2.5+ (42) | 3+ (72) |
| 3 | 3+ (106) | 2+ (56) | 3+ (86) |
| 4 | 2+ (162) | 2+ (84) | 3+ (115) |
| 5 | 2+ (219) | 1.5+ (140) | 2+ (170 |
| 6 | 2+ (266) | 1 (180) | 2+ (2270 |
| 7 | 1.5+ (310) | | 1.5+ (270) |
| 8 | 1+ (353) | | 1.5+ (296) |
| 9 | 1+ (400) | | 1.5+ (324) |
| 10 | 1+ (450) | | 1.5+ (387) |

Legend: T* = zero (pre-therapy). +refers to relative intensity of x-ray film exposed for five days to $^{32}$P containing viral DNA. Larger pluses (e.g., 3+ vs. 1+) refer to more intense and larger slot-blots on x-ray film indicating presence of more viral DNA. In order to increase sensitivity of viral measurements, various dilutions of patient sera were used, typically dilutions of 1:40, 1:200, 1:40 and 1:1,500. Confirmatory resuls were established with densitometric tracings of slot blots. Methodology was based on reagents provided by Schleicher and Schnell (materials designated No. 370 2/284). Complementary results were obtained with analysis of viral specific antigen (immunoassay for the detection of hepatitis B surface antigen in human serum or plasma) kit available from Abbott Laboratories (designated technical exhibit 83-0804/R12 dated July 1985)

As the results of my invention become known publicly and further developed and applied to additional conditions/ infections/disorders, it may well become possible to make a clinical diagnosis of dsRNA deficiency without relying on extensive laboratory date and perhaps even the scientific insight and novelty I put forth in this document. Many less obvious dsRNA-deficiency states can also exist. For example, since IFN operates naturally as a feback inhibitor of proliferative pathways (Aullo et al, *Cell,* Vol. 43, pp. 793, 1985), and since dsRNA-dependent mediators implement these events, then cells undergoing differentiations or with tumorigenic/metastaic potential may be dsRNA-deficient.

From the examples cited above, it is apparent that by interrelating biologic function (e.g., cell response to exogenous IFN) or biochemical function (e.g., elevated 2-5A synthetase) or presence of 2'-5' oligoadenylate pathway intermediates, I can readily diagnose dsRNA deficiency states and quantitate the degree of derangement by various means including:

(a) Determination of endogenous 2',5' oligoadenylate concentrations.

(b) Quantitative analysis of 2-5A concentration and molecular size of 2-5A from patient samples via high pressure liquid chromatography.

(c) Proof of biological functionality of the 2-5A synthesized in vivo in patients utilizing ribosomal RNA cleavage assays.

(d) Binding assays with 2', 5'-$p_3A_4\{^{32}P\}$-3'-pCp to determine the level of free (unbound) RNase L in patients' samples.

(e) Core-cellulose assays (affinity chromatography) with poly U-$\{^{32}P\}$-pCp to characterize the specificity of activation of RNase L by 2-5A synthesized in patient samples.

(f) Ribosomal RNA cleavage assays to determine the level of activate RNase L by 2-5A synthesized in patient samples.

(f) Ribosomal RNA cleavage assays to determine the level of activated RNase L in patients samples.

Some of these methods are described in detail in my patent applications entitled "Elaboration of Host Defense Mediators into Biological Fluid", Ser. No. 028,823 filed Aug. 12, 1987, and "Double Stranded RNA Correction of Aberrant Metabolic Pathways", Ser. No. 074,649 filed Jul. 17, 1987, which are herewith incorporated by reference.

DsRNA sufficiency states can also exist. For example, CML and hairy cell leukemia (HCL) are often responsive to IFN given as sole therapy and reflect intracellular situations of natural dsRNA sufficiency. To support this notion, I found similar levels of 2-5A synthetase-activating dsRNA in nuclei of mononuclear blood cells form untreated patients with HCL as in nuclei of IFN-treated Hela cells.

Mismatched dsRNA. While many dsRNAs can induce various lymphokines, including IFN, and activate 2-5A synthetase, not all dsRNAs have these properties. Of synthetic dsRNAs, poly(I):poly(C) is an excellent inducer of IFN and activator of 2-5A synthetase but is also very toxic. Poly(I):poly($C_{12}$,U), also referred to as "mismatched dsRNA" or Ampligen® (HEM Research, Inc., Rockville, Md., USA), contains periodic uracil residues in the polypyrimidine strand. Mismatching induces rapid biodegradation without destroying biological function. For example, poly(I-):poly($C_{12}$,U) exhibits antiviral, antitumor and immune-enhancing activity, and is nontoxic.

DsRNA As A Replacement Therapy in Broad Spectrum Vital and Cancer Therapy. Mismatched dsRNA may be particularly well-suited for chronic viral infections including ARC treatment because it is both a broad-spectrum antiviral and an immune enhancer; even at high doses it is essentially without long term toxicity. My data on 45 consecutive patients treated intraveneously with 200–250 mg of poly(I-):poly($C_{12}$,U) twice weekly showed rapid decline in virus concentration (HIV, CMV and herpes) and durable enhancement of both T and B cell immunity accompanied by improved performance with no significant side effects. In many patients, the clinical responses continue over approximately 18 months, or as long as they continued dsRNA therapy (100–400 mg twice weekly). In some cases larger doses, more frequently applied, may be necessary. Viral infections and immune lesions in AIDS patients may differ from one individual to another and no single agent can be expected to reverse all the potential clinical problems.

However, dsRNA may play a pivotal role in various treatment regimens. For example, since mismatched dsRNA displayed synergy with AZT in blocking HIV infection of T4 cells (see my co-pending application Ser. No. 028,823), mismatched dsRNA and very low dose AZT may be an important combination in early phases of infection including ARC. Both dsRNA and IL-2 enhance T cell, NK cell and LAK cell activity and thus far, where combined, I have shown that the two biologicals have displayed therapeutic synergism without added toxicity. Further, I anticipate that, insofar as IFNs enhance differentiation of B cells and monocytes, certain lymphokines may increase the ability of dsRNA to promote specific neutralizing antibodies against HIV and increase monocyte killing activity. Similarly, since retinoids increase the number of T4 cells and promote differentiation of both T and B cells with IFN, the combination of dsRNA and retinoids may provide additional benefits in ARC and AIDS. The combinations of dsRNA and thymic peptides may also have T4 cell restorative effects, especially in patients with very low T4 cell numbers. Finally, the fact that dsRNA exhibits direct antiproliferative activity against Kaposi's sarcoma cells which can be augmented by adding either IFN alpha or IL-2, suggests a new antitumor regimen in advanced disease. Control of blood cell parameters in AIDS will reveal increased CNS problems. To that end, mismatched dsRNA crosses the murine blood brain barrier in sufficient quantities to activate oligo 2'5' adenylate synthetase in brain parenchymal cells; thus, combinations of dsRNA and other agents including lymphokines which cross the blood-brain barrier will be useful in viral-related dementias. Lymphokines will be understood to include the interferons, preferably interferon alpha, the interleukins, specifically interleukin-2 (IL-2) and recombinant interleukin-2 (rIL-2), and tumor necrosis factor (TNF). Also included are lymphokine activated killer (LAK) cells formed in animals in response to exposure to a lymphokine.

When interferon (alpha) is used as the lymphokine, an amount of from 0.01 to 100,000 IRU per milliliter of the patient's body fluid is provided. When IL-2, preferably rIL-2, is the lymphokine, the amount administered lies within a range of about $10^2$ IL-2 units per kg of the patient's body weight up to a value approaching unacceptable levels of toxicity in the patient, which may be as high as $10^6$ IL-2 units. However, most effective, toxic-reaction manageable values are in the range of from about $10^3$ to about $10^4$ IL-2 per kg of body weight.

The usual amounts of dsRNA administered provide a level of from 0.1 to 1,000 micrograms dsRNA per milliliter of the patient's body fluid. The term body fluid is intended to refer to that solution of serum, salts, vitamins, etc., which circulates within the organism and bathes the tissues. When both agents (a dsRNA and a lymphokine) are administered they may be administered as a mixture, administered separately but simultaneously, or sequentially.

Administration of a dsRNA and a lymphokine "in combination" includes presentations in which both agents are administered together as a therapeutic mixture, and also procedures in which the two agents are administered separately but simultaneously.

FIG. 1 is a flow chart illustrating a typical dsRNA deficiency which leads to host morbidity and dsRNA sufficiency which leads to host recovery. Bioactive dsRNA is produced intracellularly or introduced by certain viruses (e.g., EMC) and triggers a series of enzymatic events, including lymphokine production and mediator activation, which lead to an antiviral state as well as immune cell differentiation and host recovery. DsRNA introduced by various viruses (e.g., HIV) or tumor cells can subvert this pathway by acting as an inhibitor. Physiological events can limit dsRNA production or cause production of aberrant dsRNA. Such abnormalities lead to chronic infections and hose morbidity. In HIV and other chronic viral infections, immune dysfunction can also result from an inhibitor of RNase L (shown as an alternate pathway) which is overcome by a supply of appropriately configured exogenous dsRNA.

FIG. 2A and 2B illustrate induction of 2'5' oligoadenylate synthetase by mismatched dsRNA in MNC or a CML patient. A CML patient was treated with IFN alone for seven days (FIG. 2A), then with mismatched dsRNA and IFN (FIG. 2B). At times before and during treatment, synthetase activity was measured in Ficoll-purified MNC.

FIG. 3A is a photograph of polyacrylamide gel electrophoresis plates showing the indicate number of tracks and bands or zones along each track. Elevated activity of RNase L associated with novel cleavage products in MNC of a CML patient are illustrated on this plate. Hungarian L929 cells which supply rRNA but no RNase L, are deposited under the terms of the Budapest Convention at the American Type Culture Collection as ATCC No. CRL 9659; L929 cells as deposited as CCL 1 and MNC from the CML patient were prepared according to Kariko and Ludwig and Silverman et al, then RNase L from the MNC was measured as described in my co-pending application Ser. No. 074,649 filed Jul. 17, 1987, the disclosure of which is hereby incorporated by reference.

Figure 3B:
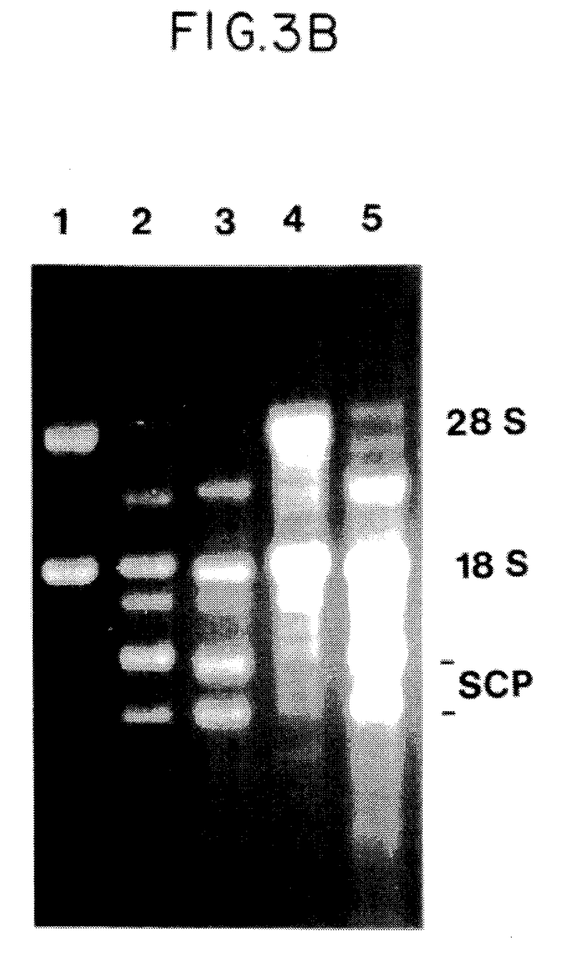

FIG. 3B is also a photograph of a polyacrylamide gel electrophoresis plates showing the presence of an RNase L inhibitory factor in PBMC extracts of an ARC patient as determined in the rRNA cleavage assay. Extracts of L929 cells (which supply both RNase L and rRNA) and MNC were prepared according to Kariko and Ludwig and Silverman et al. respectively.

Lane 1: 18 µl L929 cell extract (150 µg total protein) was incubated in the presence of 4 µl NP40 buffer used for MNC lysis plus 5.5 µl water.

Lane 2: identical to Lane 1, except that in lieu of water, 5.5 µl of $5\times10^{-8}$ M authentic P3A3 was added to incubations.

Lane 3: identical to Lane 1 except that 5.5 µl of TCA-soluble extract from MNC extract (100 µg total protein) from an ARC patient was added prior to incubation.

Lane 4: 18 µl L929 cell extract was incubated with 4 µl MNC extract from an ARC patient (100 µg total protein) and 5.5 µl water.

Lane 5: 18 µl L929 cell extract was incubated with 4 µl MNC extract from a healthy individual (100 µg total protein) and 5.5 µl water. 28S and 18S rRNA as well as normal levels of 2'5'A activated RNase L specific cleavage products are indicated.

What is claimed is:

1. A method of treating viral hepatitis comprising administering to a person having vital hepatitis an effective amount of a mismatched double-stranded RNA of the formula $rI_n \cdot r(C_{11-14}, U)_n$.

2. The method of claim 1 in which the mismatched dsRNA is administered in an amount which will result in a level of from 1 to 1,000 micrograms per milliliter of the patient's body fluid.

3. The method of claim 1 in which the amount administered is 400 mg per week.

* * * * *